(12) United States Patent
Rojer

(10) Patent No.: US 8,288,518 B2
(45) Date of Patent: Oct. 16, 2012

(54) REARRANGED SQUAMOUS CELL CARCINOMA ANTIGEN GENES

(75) Inventor: Eva Rojer, Gothenburg (SE)

(73) Assignee: Canag Diagnostics AG, Gothenburg (SE)

( * ) Notice: Subject to any disclaimer, the term of this patent is extended or adjusted under 35 U.S.C. 154(b) by 149 days.

(21) Appl. No.: 12/552,557

(22) Filed: Sep. 2, 2009

(65) Prior Publication Data

US 2010/0062514 A1    Mar. 11, 2010

Related U.S. Application Data

(60) Division of application No. 10/661,742, filed on Sep. 12, 2003, now abandoned, which is a continuation of application No. PCT/SE02/00512, filed on Mar. 15, 2002.

(30) Foreign Application Priority Data

Mar. 15, 2001 (SE) ........................ 0100938

(51) Int. Cl.
*C07H 21/04* (2006.01)
(52) U.S. Cl. ..................................... 536/23.4
(58) Field of Classification Search ........................ None
See application file for complete search history.

(56) References Cited

U.S. PATENT DOCUMENTS 5,306,811 A    4/1994    Duffy

FOREIGN PATENT DOCUMENTS

WO          0102603        1/2001

OTHER PUBLICATIONS

Röjer et al., Tumor Biol., 2003, 24: 46-52.*
Schick et al. "The reactive site loop of the serpin SCCA1 is essential for crysteine proteinase inhibition"; Proc. Natl. Acad. Sci., USA; vol. 95; ogs,L 13465-13470, Nov. 1998.
Schick et al. "Squamous Cell Carcinoma Antigen 2 Is a Novel Serpin That Inhibits the Chymotrypsin-like Proteinases Cathepsin G and Mast Cell Chymase"; Journal of Biological Chemistry; vol. 272, No. 3, Jan. 17, 1997; pp. 1849-1855.
Wobbes et al. "The Squamous Cell Carcinoma Tumor Marker in Mammary Carcinoma: Comparison of Polyclonal versus Monoclonal Antibody-Based Assays"; Department of General Surgery and Obstetrics and Gynecology, Universith Hospital Nijmegen, The Netherlands; Oncology 1990; pp. 14-18.
Greenbaum et al., Genome Biology, 2003, vol. 4(9), pp. 117.1-117.8.
Alberts et al., Molecular Biology of the Cell, 3rd Edition, 1994, p. 465.
Mallampalli et al., Biochem. J. 1996, vol. 38, pp. 333-341.
Fu et al., EMBO journal, 1996, vol. 15, pp. 4392-4402.
Roijer et al., Tumor Biol. 2003, 24:46-52.
Nawata et al., Electrophoresis, 1999, 20:614-617.
Matsuda et al., Cancer, 1990, 65:2261-2265.
Cataltepe et al., Clin. Chim. Acta, 2000, 295:107-127.
English translation of DE 19742725, published Sep. 26, 1997.
Derwent GeneSeq database of patented sequences, Acc. No. AAY25928 and Derwent GeneSeq database for patented sequences, Acc. No. AAY25927, Oct. 6, 1999.
Suminami et al. "Novel forms of squamous cell carcinoma antigen transcripts produced by alternative splicing"; Yamaguchi University School of Medicine, Japan; pp. 122-126, 2001.

* cited by examiner

*Primary Examiner* — Hong Sang
(74) *Attorney, Agent, or Firm* — Gesmer Updegrove LLP

(57) ABSTRACT

The present invention relates to a SCCA1/SCCA2 fusion protein; plasmid containing the same; antibodies of said fusion protein; methods for detecting said protein; methods for diagnosing the presence or absence of SCC by determining the presence of SCCA1/SCCA2 fusion protein.

10 Claims, 7 Drawing Sheets

A
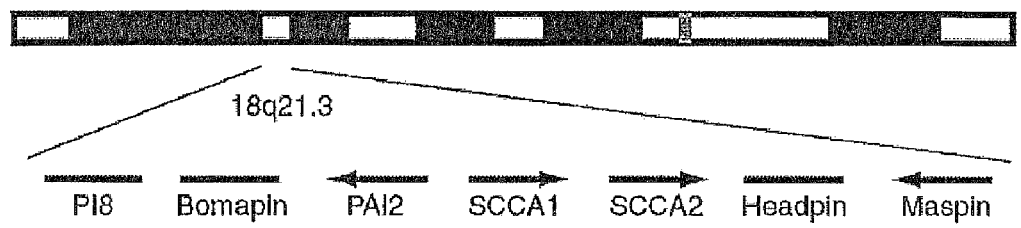
B
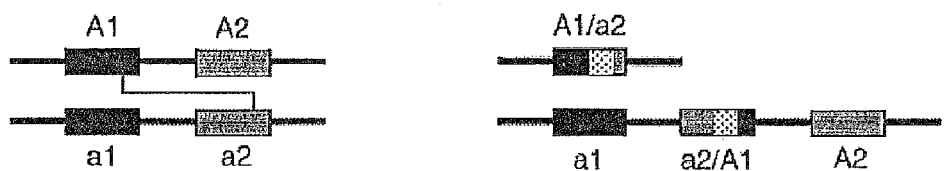
C
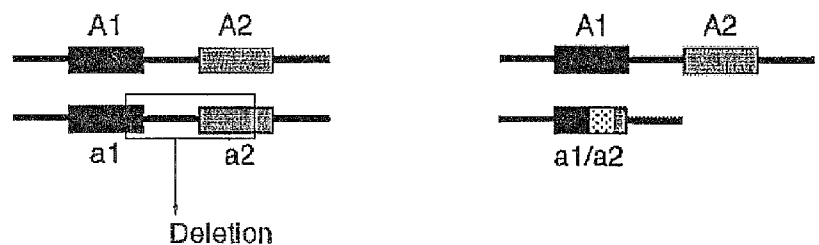
Fig. 1A-C

```
SCCA1 I1-ATGAATTCAC TCAGTGAAGC CAACACCAAG TTCATGTTCG ACCTGTTCCA ACAGTTCAGA
SCCA2 I1-ATGAATTCAC TCAGTGAAGC CAACACCAAG TTCATGTTCG ATCTGTTCCA ACAGTTCAGA

AAATCAAAAG AGAACAACAT CTTCTATTCC CCTATCAGCA TCACATCAGC ATTAGGGATG
AAATCAAAAG AGAACAACAT CTTCTATTCC CCTATCAGCA TCACATCAGC ATTAGGGATG

GTCCTCTTAG GAGCCAAAGA CAACACTGCA CAACAGATTA AGAAG -I2- GTTCT TCACTTTGAT
GTCCTCTTAG GAGCCAAAGA CAACACTGCA CAACAAATTA GCAAG -I2- GTTCT TCACTTTGAT

CAAGTCACAG AGAACACCAC AGGAAAAGCT GCAACATATC AT -I3- GTTGATAG GTCAGGAAAT
CAAGTCACAG AGAACACCAC AGAAAAAGCT GCAACATATC AT -I3- GTTGATAG GTCAGGAAAT

GTTCATCACC AGTTTCAAAA GCTTCTGACT GAATTCAACA AATCCACTGA TGCATATGAG
GTTCATCACC AGTTTCAAAA GCTTCTGACT GAATTCAACA AATCCACTGA TGCATATGAG

CTGAAGATCG CCAACAAGCT CTTCGGAGAA AAAACGTATC TATTTTTACA G -I4- GAATATTTA
CTGAAGATCG CCAACAAGCT CTTCGGAGAA AAGACGTATC AATTTTTACA G -I4- GAATATTTA

GATGCCATCA AGAAATTTTA CCAGACCAGT GTGGAATCTG TTGATTTTGC AAATGCTCCA
GATGCCATCA AGAAATTTTA CCAGACCAGT GTGGAATCTA CTGATTTTGC AAATGCTCCA

GAAGAAAGTC GAAAGAAGAT TAACTCCTGG GTGGAAAGTC AAACGAATG -I5- AAAAAATTAAA
GAAGAAAGTC GAAAGAAGAT TAACTCCTGG GTGGAAAGTC AAACGAATG -I5- AAAAAATTAAA

AACCTAATTC CTGAAGGTAA TATTGGCAGC AATACCACAT TGGTTCTTGT GAACGCAATC
AACCTATTTC CTGATGGGAC TATTGGCAAT GATACGACAC TGGTTCTTGT GAACGCAATC

TATTTCAAAG GGCAGTGGGA GAAGAAATTT AATAAAGAAG ATACTAAAGA GGAAAAATTT
TATTTCAAAG GGCAGTGGGA GAATAAATTT AAAAAAGAAA ACACTAAAGA GGAAAAATTT

TGGCCAAACA AG -I6- AATACATA CAAGTCCATA CAGATGATGA GGCAATACAC ATCTTTTCAT
TGGCCAAACA AG -I6- AATACATA CAAATCTGTA CAGATGATGA GGCAATACAA TTCCTTTAAT

TTTGCCTCGC TGGAGGATGT ACAGGCCAAG GTCCTGGAAA TACCATACAA AGGCAAAGAT
TTTGCCTTGC TGGAGGATGT ACAGGCCAAG GTCCTGGAAA TACCATACAA AGGCAAAGAT

CTAAGCATGA TTGTGTTGCT GCCAAATGAA ATCGATGGTC TCCAGAAG -I7- CTTGAAGAGAAA
CTAAGCATGA TTGTGCTGCT GCCAAATGAA ATCGATGGTC TGCAGAAG -I7- CTTGAAGAGAAA

CTCACTGCTG AGAAATTGAT GGAATGGACA AGTTTGCAGA ATATGAGAGA GACACGTGTC
CTCACTGCTG AGAAATTGAT GGAATGGACA AGTTTGCAGA ATATGAGAGA GACATGTGTC

GATTTACACT TACCTCGGTT CAAAGTGGAA GAGAGCTATG ACCTCAAGGA CACGTTGAGA
GATTTACACT TACCTCGGTT CAAAATGGAA GAGAGCTATG ACCTCAAGGA CACGTTGAGA

ACCATGGGAA TGGTGGATAT CTTCAATGGG GATGCAGACC TCTCAGGCAT GACCGGGAGC
ACCATGGGAA TGGTGAATAT CTTCAATGGG GATGCAGACC TCTCAGGCAT GACCTGGAGC

CGCGGTCTCG TGCTATCTGG AGTCCTACAC AAGGCCTTTG TGGAGGTTAC Agaggaggga
cACGGTCTCT CAGTATCTAA AGTCCTACAC AAGGCCTTTG TGGAGGTCAC Tgaggaggga gcagaagctg cagctgccac cgctgtagta ggattcggat catcacctac ttcaactAAT
gtggaagctg cagctgccac cgctgtagta gtagtcgaat tatcatctcc ttcaactAAT GAAGAGTTCC ATTGTAATCA CCCTTTCCTA TTCTTCATAA GGCAAAATAA GACCAACAGC
GAAGAGTTCT GTTGTAATCA CCCTTTCCTA TTCTTCATAA GGCAAAATAA GACCAACAGC ATCCTCTTCT ATGGCAGATT CTCATCCCCG TAG (SEQ ID NO:12)
ATCCTCTTCT ATGGCAGATT CTCATCCCCA TAG (SEQ ID NO:13)
```

FIG. 2

SCCA1 MNSLSEANTK FMFDLFQQFR KSKENNIFYS PISITSALGM VLLGAKDNTA
SCCA2 MNSLSEANTK FMFDLFQQFR KSKENNIFYS PISITSALGM VLLGAKDNTA

QQI<u>K</u>KVLHFD QVTENTT<u>G</u>KA ATY HVDRSGN VHHQFQKLLT EFNKSTDAYE
QQI<u>S</u>KVLHFD QVTENTT<u>E</u>KA ATY HVDRSGN VHHQFQKLLT EFNKSTDAYE

LKIANKLFGE KTY<u>L</u>FLQ EYL DAIKKFYQTS VES<u>V</u>DFANAP EESRKKINSW
LKIANKLFGE KTY<u>Q</u>FLQ EYL DAIKKFYQTS VES<u>T</u>DFANAP EESRKKINSW

VESQTN EKIK NL<u>IPEGNIGS</u> <u>N</u>TTLVLVNAI YFKGQWE<u>KK</u>F <u>NKED</u>TKEEKF
VESQTN EKIK NL<u>FPDGTIGN</u> <u>D</u>TTLVLVNAI YFKGQWE<u>N</u>KF <u>KKEN</u>TKEEKF

WPNK NTYKS<u>I</u> QMMRQY<u>TSFH</u> FA<u>S</u>LEDVQAK VLEIPYKGKD LSMIVLLPNE
WPNK NTYKS<u>V</u> QMMRQY<u>NSFN</u> FA<u>L</u>LEDVQAK VLEIPYKGKD LSMIVLLPNE

IDGLQ KLEEK LTAEKLMEWT SLQNMRET<u>R</u>V DLHLPRFK<u>VE</u> ESYDLKDTLR
IDGLQ KLEEK LTAEKLMEWT SLQNMRET<u>C</u>V DLHLPRFK<u>ME</u> ESYDLKDTLR

TMGMV<u>D</u>IFNG DADLSGMT<u>GS</u> <u>RGLVLSG</u>VLH KAFVEVT<u>EEG</u> <u>AEAAAA</u> TAVV
TMGMV<u>N</u>IFNG DADLSGMT<u>WS</u> <u>HGLSVSK</u>VLH KAFVEVT<u>EEG</u> <u>VEAAAA</u> TAVV

<u>GFGSSPAST</u> N EEF<u>H</u>CNHPFL FFIRQNKTNS ILFYGRFSSP (SEQ ID NO:14)
<u>VVELSSPST</u> N EEF<u>C</u>CNHPFL FFIRQNKTNS ILFYGRFSSP (SEQ ID NO:15)

FIG. 3

SCCA1/A2 cDNA SEQUENCE

-I1 - ATGAATTCAC TCAGTGAAGC CAACACCAAG TTCATGTTCG ACCTGTTCCA ACAGTTCAGA

AAATCAAAAG AGAACAACAT CTTCTATTCC CCTATCAGCA TCACATCAGC ATTAGGGATG

GTCCTCTTAG GAGCCAAAGA CAACACTGCA CAACAGATTA AGAAG -I2- GTTCT TCACTTTGAT

CAAGTCACAG AGAACACCAC AGGAAAAGCT GCAACATATC AT -I3- GTTGATAG GTCAGGAAAT

GTTCATCACC AGTTTCAAAA GCTTCTGACT GAATTCAACA AATCCACTGA TGCATATGAG

CTGAAGATCG CCAACAAGCT CTTCGGAGAA AAAACGTATC TATTTTTACA G -I4- GAATATTTA

GATGCCATCA AGAAATTTTA CCAGACCAGT GTGGAATCTG TTGATTTTGC AAATGCTCCA

GAAGAAAGTC GAAAGAAGAT TAACTCCTGG GTGGAAAGTC AAACGAATG -I5- A AAAAATTAAA

AACCTAATTC CTGAAGGTAA TATTGGCAGC AATACCACAT TGGTTCTTGT GAACGCAATC

TATTTCAAAG GGCAGTGGGA GAAGAAATTT AATAAAGAAG ATACTAAAGA GGAAAAATTT

TGGCCAAACA AG -I6- AATACATA CAAGTCCATA CAGATGATGA GGCAATACAC ATCTTTTCAT

TTTGCCTCGC TGGAGGATGT ACAGGCCAAG GTCCTGGAAA TACCATACAA AGGCAAAGAT

CTAAGCATGA TTGTGTTGCT GCCAAATGAA ATCGATGGTC TCCAGAAG -I7- CT TGAAGAGAAA

CTCACTGCTG AGAAATTGAT GGAATGGACA AGTTTGCAGA ATATGAGAGA

GACATGTGTC GATTTACACT TACCTCGGTT CAAAATGGAA GAGAGCTATG

ACCTCAAGGA CACGTTGAGA ACCATGGGAA TGGTGAATAT CTTCAATGGG

GATGCAGACC TCTCAGGCAT GACCTGGAGC CACGGTCTCT CAGTATCTAA

AGTCCTACAC AAGGCCTTTG TGGAGGTCAC T*gaggaggga gtggaagctg*

*cagctgccac cgctgtagta gtagtcgaat tatcatctcc tt*caactAAT

GAAGAGTTCT GTTGTAATCA CCCTTTCCTA TTCTTCATAA GGCAAAATAA

GACCAACAGC ATCCTCTTCT ATGGCAGATT CTCATCCCCA TAG (SEQ ID NO:16)

FIG. 4

SCCA1A2 amino acid sequence

MNSLSEANTK FMFDLFQQFR KSKENNIFYS PISITSALGM VLLGAKDNTA

QQIK KVLHFD QVTENTTGKA ATY HVDRSGN VHHQFQKLLT EFNKSTDAYE

LKIANKLFGE KTYLFLQ EYL DAIKKFYQTS VESVDFANAP EESRKKINSW

VESQTN EKIK NLIPEGNIGS NTTLVLVNAI YFKGQWEKKF NKEDTKEEKF

WPNK NTYKSI QMMRQYTSFH FASLEDVQAK VLEIPYKGKD LSMIVLLPNE

IDGLQK LEEK LTAEKLMEWT SLQNMRETCV DLHLPRFKME ESYDLKDTLR

TMGMVNIFNG DADLSGMTWS HGLSVSKVLH KAFVEVTEEG VEAAAA TAVV

VVELSSPST N EEFHCNHPFL FFIRQNKTNS ILFYGRFSSP  (SEQ ID NO: 1)

FIG. 5

REARRANGED SQUAMOUS CELL CARCINOMA ANTIGEN GENES

PRIORITY INFORMATION

This application is a divisional of U.S. patent application Ser. No. 10/661,742 filed on Sep. 12, 2003 which is continuation of PCT patent application serial number PCT/SE02/00512 filed Mar. 15, 2002, which claims priority to Swedish Patent Application No. 0100938-0 filed Mar. 15, 2001 all of which are incorporated herein in their entirety.

BACKGROUND OF THE INVENTION

1. Field of Invention

The present invention relates to a fusion gene found in squamous cell carcinomas, detection of the rearrangement and monoclonal antibodies specific for SCCA1, SCCA1/A2, SCCA2/A1 and SCCA2.

2. Description of the Prior Art

Squamous cell carcinoma antigen (SCCA) is a serological marker for squamous cell carcinomas (SCC) of the uterine cervix, lung, head and neck, vulva, and esophagus (1, 2). It was originally purified from the TA-4 complex from human cervical squamous cell carcinoma, with a molecular weight of 42-48 kDa (1, 3). The antigen consists of more than 10 proteins and iso-electric focusing of the antigen reveals two subfractions, an acidic (pI<6.25) and a neutral (pI≧6.25) isoform (4). The difference in molecular weight is probably due to modification (5).

Cloning of the cDNA of SCCA shows that it belongs to the family of serine protease inhibitors (serpins) (6). Further cloning of the genomic region on chromosome 18q21.3 reveals two tandemly arrayed genes (7). The more telomeric one, the original SCCA, was designated SCCA1, whereas the more centromeric one was designated SCCA2 (FIG. 1A). They both contain eight exons and the putative intron-exon boundaries, splice sites, initiation codons, and terminal codons are identical. They are 98% identical at the nucleotide level (FIG. 2) and 92% identical at the amino acid level (FIG. 3). The deduced pI value shows that the neutral isoform is coded by SCCA1, and the acidic isoform by SCCA2. Alternatively spliced variant mRNA from both the genes have been found resulting in proteins 52 and 21 amino acids shorter (5).

In humans the serpins map to one of two chromosomal clusters. PI6, PI9 and ELNAH2 map to 6p25, whereas PI8, Bomapin, PAI2, SCCA1, SCCA2, Headpin and Maspin map to 18q21.3 (FIG. 1A) (7-12). These clusters are supposed to have arisen via two independent interchromosomal duplications and several rounds of intrachromosomal duplications (9). The chromosome region 18q has often been reported as a region with high frequency of rearrangements (9, 13-16). The targets and functions of serpins are not fully understood. For most, the primary functions are regulation of proteolytic events associated with coagulation, fibrinolysis, apoptosis and inflammation, but alternative functions such as hormone transport and blood pressure regulation have been reported (17-24).

Although SCCA1 and SCCA2 are nearly identical they differ in their reactive site loops (FIGS. 2 and 3). SCCA1 inhibits the papain-like cystein proteinases cathepsin S, K, and L (25, 26) while SCCA2 inhibits the chymotrypsin-like serine proteinases cathepsin G and mast cell chymase (27). Studies of the reactive site loop (RSL) of SCCA1 show that the RSL is essential for cystein proteinase inhibition (28). The variable portion of the RSL dictates the specificity of the target proteinases shown by RSL swap mutants of SCCA1 and SCCA2 and single mutants (28, 29). It is likely that serpins utilize a common RSL-dependent mechanism to inhibit both serine and cystein proteinases.

The biological role of SCCA1 and SCCA2 are not fully understood. They are considered to be inhibitory serpins. Data suggest that SCCA1 is involved in apoptosis and expression makes cancer cells resistant to several killing mechanisms by inhibition of apoptosis (30). The role of SCCA2 expression in cancer cells is still unclear. In normal tissue SCCA antigen may have some specific role during epidermal maturation (5).

Recent studies using discriminatory monoclonal antibodies and polymerase chain reaction (PCR) have shown that both SCCA1 and SCCA2 are expressed in the suprabasal layers of the stratified squamous epithelium of the tongue, tonsil, esophagus, uterine cervix and vagina, Hassall's corpuscles of the thymus, some area of the skin and in the stratified columnar epithelium of the conducting airways (31). In squamous cell carcinomas of the lung and head and neck, SCCA1 and SCCA2 were co-expressed in moderately and well-differentiated tumors. In contrast to previous studies using nondiscriminatory antibodies, these data show that there were no differential expression between SCCA1 and SCCA2 in normal and malignant tissue. Previous results have shown that SCCA2 was only detected at the peripheral parts of the tumor (32). This discrepancy may be due to differences between immunohistochemical techniques and antibody specificities (31). It has been reported that false positive results may often be caused by contamination with saliva or sweat during assay procedure (1). Cataltepe et al. suggest that the SCCAs in saliva are derived from the squamous epithelial cells lining mucosal surfaces of the upper digestive tract (31).

Normally, SCCA1 and SCCA2 are detected in the cytoplasm of squamous epithelial cells (31), but not in the circulation (33). The antigen, which appears in the serum of patients with SCC, may be a function of SCCA-over-production by tumor cells and their normal turn over (34). It has been reported that the SCCA detected in serum by using antibody radioimmuno-assay or RT-PCR is mainly SCCA2 (1, 35, 36) but other studies using PCR indicate that both antigens can be amplified and detected in patient samples (37).

Serum concentrations present in patients with SCC are correlated to the clinical stage and to the degree of histological differentiation of the tumor (1). For cervical cancer several studies show a correlation between the pretreatment values and the clinical outcome (1, 38-43). Studies also show a correlation between high SCCA levels and tumor volume. Recurrence or progressive disease could be detected several months before clinical evidence (39). Similar results are seen for squamous cell carcinomas of the lung, vulva, head and neck and esophagus (1, 2, 44, and 45). In all these studies, they have measured the total SCCA level. Recently a new sELISA was developed using discriminating antibodies for SCCA1 and SCCA2 (33).

SUMMARY OF THE INVENTION

The present invention provides the detection of a fusion gene consisting of SCCA1 and SCCA2. This fusion gene has now been found in SCC cell-lines of different origin (cervix, lung and pharynx). The invention also provides methods for establishment of specific immunological reagents for determination/detection of the fusion protein.

One fusion protein is defined by the following amino acid sequence (SEQ ID NO: 1)

```
MNSLSEANTK FMFDLFQQFR KSKENNIFYS PISITSALGM
VLLGAKDNTA QQIKKVLHFD QVTENTTGKA ATYHVDRSGN
VHHQFQKLLTE FNKSTDAYE LKIANKLFGE KTYLFLQEYL
DAIKKFYQTS VESVDFANAP EESRKKINSW VESQTNEKIK
NLIPEGNIGS NTTLVLVNAI YFKGQWEKKF NKEDTKEEKF
WPNKNTYKSI QMMRQYTSFH FASLEDVQAK VLEIPYKGKD
LSMIVLLPNE IDGLQKLEEK LTAEKLMEWT SLQNMRETCV
DLHLPRFKME ESYDLKDTLR TMGMVNIFNG DADLSGMTWS
HGLSVSKVLH KAFVEVTEEG VEAAAATAVV VVELSSPSTN
EEFCCNHPFL FFIRQNKTNS ILFYGRFSSP
``` based upon the DNA sequence (SEQ ID NO: 2)

```
ATGAATTCAC TCAGTGAAGC CAACACCAAG TTCATGTTCG
ACCTGTTCCA ACAGTTCAGA AAATCAAAAG AGAACAACAT
CTTCTATTCC CCTATCAGCA TCACATCAGC ATTAGGGATG
GTCCTCTTAG GAGCCAAAGA CAACACTGCA CAACAGATTA
AGAAGGTTCT TCACTTTGAT CAAGTCACAG AGAACACCAC
AGGAAAAGCT GCAACATATC ATGTTGATAG GTCAGGAAAT
GTTCATCACC AGTTTCAAAA GCTTCTGACT GAATTCAACA
AATTCCACTGA TGCATATGAG CTGAAGATCG CCAACAAGCT
CTTCGGAGAA AAAACGTATC TATTTTTACA GGAATATTTA
GATGCCATCA AGAAATTTTA CCAGACCAGT GTGGAATCTG
TTGATTTTGC AAATGCTCCA GAAGAAAGTC GAAAGAAGAT
TAACTCCTGG GTGGAAAGTC AAACGAATGA AAAAATTAAA
AACCTAATTC CTGAAGGTAA TATTGGCAGC AATACCACAT
TGGTTCTTGT GAACGCAATC TATTTCAAAG GGCAGTGGGA
GAAGAAATTT AATAAAGAAG ATACTAAAGA GGAAAAATTT
TGGCCAAACA AGAATACATA CAAGTCCATA CAGATGATGA
GGCAATACAC ATCTTTTCAT TTTGCCTCGC TGGAGGATGT
ACAGGCCAAG GTCCTGGAAA TACCATACAA AGGCAAAGAT
CTAAGCATGA TTGTGTTGCT GCCAAATGAA ATCGATGGTC
TCCAGAAGCT TGAAGAGAAA CTCACTGCTG AGAAATTGAT
GGAATGGACA AGTTTGCAGA ATATGAGAGA GACATGTGTC
GATTTACACT TACCTCGGTT CAAAATGGAA GAGAGCTATG
ACCTCAAGGA CACGTTGAGA ACCATGGGAA TGGTGAATAT
CTTCAATGGG GATGCAGACC TCTCAGGCAT GACCTGGAGC
CACGGTCTCT CAGTATCTAA AGTCCTACAC AAGGCCTTTG
TGGAGGTCAC TGAGGAGGGA GTGGAAGCTG CAGCTGCCAC
CGCTGTAGTA GTAGTCGAAT TATCATCTCC TTCAACTAAT
GAAGAGTTCT GTTGTAATCA CCCTTTCCTA TTCTTCATAA
GGCAAAATAA GACCAACAGC ATCCTCTTCT ATGGCAGATT
CTCATCCCCA TAGATGCAAT TAGTGTGTCA CT
```

BRIEF DESCRIPTION OF THE DRAWINGS

FIGS. 1A-1C show the chromosome 18 rearrangement.

FIG. 2 shows the alignment of the coding DNA regions, exon 2-8 of SCCA1 and SCCA2. Intron positions are indicated as -Ix-. Differences between the genes are indicated in bold. The regions coding for reactive site loops are shown in lower-case letters. Underlining shows primer (Table 1) positions.

FIG. 3 shows the alignment of protein sequences of SCCA1 and SCCA2. Intron positions are indicated with dotted lines. Differences between the proteins are underlined. Boxes show the reactive site loops.

FIG. 4 shows nucleotide coding DNA region, exon 2-8 of the rearranged SCCA1/SCCA2. Sequences derived from SCCA1 are shown in normal style while sequences derived from SCCA2 are shown in bold. Intron positions are indicated as -Ix-. Differences between the genes are underlined. The region coding for reactive site loop is shown in lower-case letters.

FIG. 5 shows the protein sequence of the SCCA1/SCCA2 fusion protein. Amino acids derived from SCCA1 are shown in normal letters. Amino acids derived from SCCA2 are shown in bold letters. Intron positions are indicated with dotted lines. Differences between the proteins are underlined. The reactive site loop is marked with a box.

DETAILED DESCRIPTION OF THE INVENTION

Figure 6:
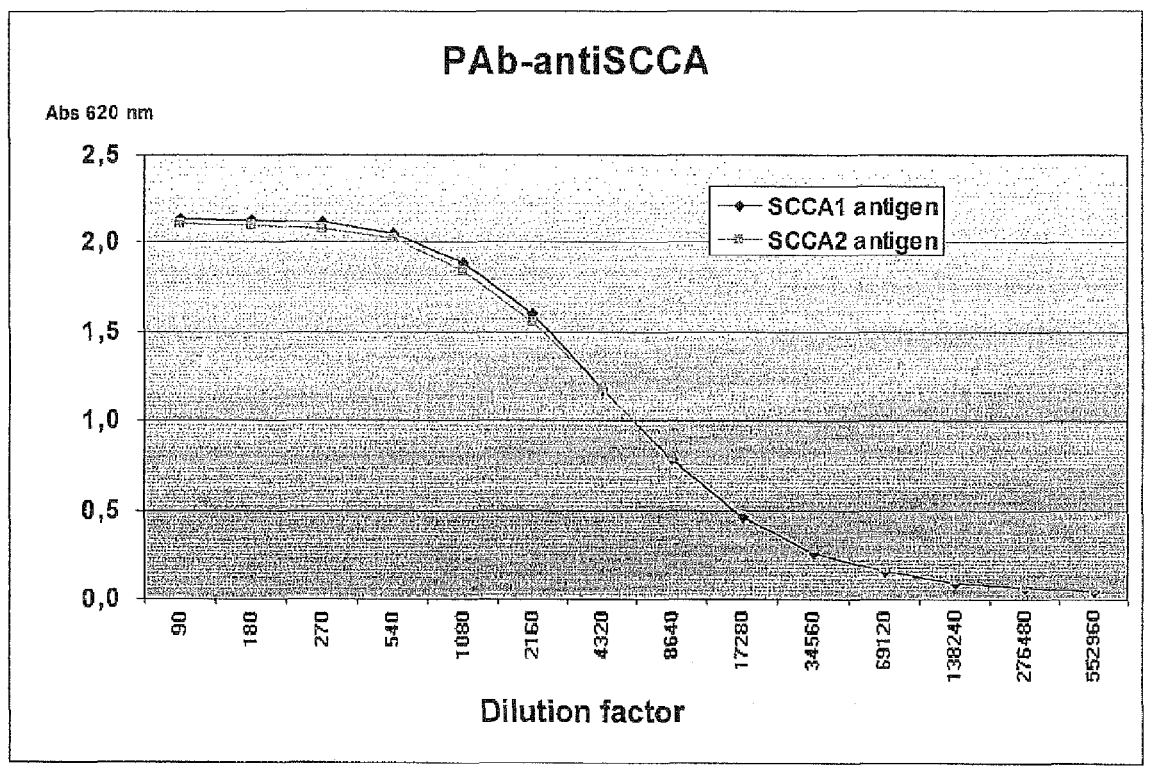
FIG. 6 is a graph showing the titer of pAB to SCC antigen.

The fusion gene (FIG. 4) was found by sequencing cDNA from SCC cell lines.

| Cell line | Origin | SCCA1 | SCCA2 |
|---|---|---|---|
| CaSki | Cervix | normal | A1/A2 |
| C4I | Cervix | normal | normal |
| A549 | Lung | N.A. | A1/A2 |
| CaLu3 | Lung | normal | normal |
| SkMES | Lung | normal | normal |
| RPMI2650 | Pharynx | N.A. | A1/A2 |

According to the sequence swift from SCCA1 to SCCA2, the DNA breakpoint would be in intron 7 (FIG. 2). The gene should consequently be controlled via the promoter region of SCCA1 but producing a protein with SCCA2-specificity.

The fusion genes are cloned and kept as plasmid-constructs as well as transformed into different *E. coli* strains.

A plasmid, pGEX6P-3 SCCA1/A2, containing the fusion gene has been deposited with European Collection of Cell Cultures on the 14th of Mar., 2001, under deposition number ECACC 01031315.

Fusion protein has been produced and complex binding studies show substrate binding of the fusion gene to Cathepsin G but not to Cathepsin L.

The fusion gene can be detected by Southern blot analysis of tumor DNA. The fusion gene can also be detected by PCR analysis as well as by cDNA cloning and sequencing.

Example 1

Cloning of SCCA 1.1. PCR Amplification mRNA from the cell-lines Caski (cervix), C4-I (cervix), A549 (lung), CaLu3 (lung), SkMes (lung), and RPMI2650 (pharynx) was prepared using QuickPrep Micro mRNA Purification kit (Pharmacia) and cDNA was prepared using First-Strand cDNA Synthesis kit (Pharmacia). A 1218 bp DNA fragment covering the coding sequence of SCCA was amplified by PCR in a 100 μl reaction containing 10 mM Tris-HCl pH 8.85, 25 mM KCl, 5 mM $(NH_4)_2SO_4$, 2 mM $MgSO_4$ (Boehringer), 0.2 mM dNTP (Pharmacia), 10 μM SCCA 1-7F (DNA sequences for all primers are shown in Table 1), 10 μM SCCA 391-397B, 2 μl cDNA and 2.5 U Pwo-polymerase (Boehringer). After denaturing samples for 5 min at 96° C. a total of 30 cycles were performed, each consisting of denaturation for 15 sec at 96° C., annealing for 15 sec at 60° C., and extension for 30 sec at 72° C. The PCR reaction was completed by a final extension for 10 min at 72° C.

TABLE 1

PCR-primers

| Primer name | Sequence |
|---|---|
| 1. SCCA 1-7F | 5'-CGGGATCCATGAATTCACTCAGTGAAGCC-3' (SEQ ID NO: 3) |
| 2. SCCA 391-397B | 5'-GAGCTCGAGTCTCATCAGTGACAGACTAATTGCATCTA-3' (SEQ ID NO: 4) |
| 3. SCCA 266-273F | 5'-TGGAATGGACAAGTTTGCAG-3' (SEQ ID NO: 5) |
| 4. SCCA1 323-329B | 5'-GTAGGACTCCAGATAGCAC-3' (SEQ ID NO: 6) |
| 5. SCCA2 319-324F | 5'-TGGAGCCACGGTCTCTCAG-3' (SEQ ID NO: 7) |
| 6. SCCA2 357-363B | 5'-ATTAGTTGAAGGAGATGATAATTC-3' (SEQ ID NO: 8) |
| 7. SCCA1 ex7 | 5'-AATACATACAAGTCCA-3' (SEQ ID NO: 9) |
| 8. SCCA2 ex8 | 5'-GGACTTTAGATACTGA-3' (SEQ ID NO: 10) |

1.2. Detection of SCCA1 and SCCA2

Presence of SCCA1 in PCR products were detected by cleavage with restriction enzyme SacII, resulting in two fragments, 245 and 973 bp, respectively, or by SCCA1-specific PCR using the primers SCCA1-7F and SCCA1 323-329B in a standard PCR reaction (75 mM Tris-HCl pH 8.8, 20 mM $(NH_4)_2SO_4$, 0.01% Tween 20, 2 mM $MgCl_2$, 0.2 mM dNTP, 10 μM of each primer, template, and 0.025 U/μl reaction Taq Polymerase; after denaturing samples for 5 min at 96° C. a total of 30 cycles were performed, each consisting of denaturation for 15 sec at 96° C., annealing for 15 sec at optimal annealing temperature, and extension for 30 sec at 72° C. The PCR reaction was completed by a final extension for 10 min at 72° C.), Ta=50° C., resulting in a 997 bp fragment. Presence of SCCA2 were detected by standard PCR using SCCA 1-7F and an SCCA2-specific primer, SCCA2 357-363B, Ta=60° C., giving a 1090 bp fragment.

1.3. Cloning

PCR-products were cloned using PCR-Script Amp cloning kit (Stratagene). Colony screening was performed by PCR as described in 1.2 above. Plasmid-DNA was prepared from selected clones containing SCCA1 or SCCA2 using Wizard Plus Minipreps DNA Purification System (Promega).

1.4. DNA Sequencing

Clones were sequenced using ABI Prism BigDye Terminator Cycle Sequencing (PE Biosystems). Samples were run on an ABI Prism 310.

1.5. Recloning

Selected clones were recloned into the expression vector pGEX-6P-3 (Pharmacia). Fragments were excised from the PCR-Script Amp vector using BamHI and XhoI and ligated into the expression vector in a 10 μl reaction containing 1×OPA, 1 mM ATP, 50 ng cleaved vector, SCCA insert corresponding to a moles-of-ends vector: insert ratio of 1:5-1:8, and 7.5-10 U T4DNAligase (all from Pharmacia). Reaction tubes were incubated at 10° C. overnight and inactivated for 10 min at 65° C. 2-4 μl of the reaction was transformed into *E. coli* JM109 (46). Plasmid-DNA from selected clones was then transformed into *E. coli* BL21 for protein expression.

1.6. Maintenance of Cloned Gene

Plasmid-DNA (pGEX-6P-3 containing the SCCA1/A2 fusion gene) in a 10 mM Tris-HCL pH 8.0 buffer solution is stored in −80° C. For resuming protein expression, plasmid-DNA is transformed into competent *E. Coli* BL21 according to Sambrook et al. (p 1.82-1.84 in Sambrook, J., Fritsch, E. F. & Maniatis, T. (1989) Cold Spring Harbor Laboratory Press, Cold Spring Harbor, N.Y.). For preparation of more plasmid-DNA, transformation into *E. Coli* JM109 is preferred.

Example 2

Protein Expression and Purification 2.1. Protein Expression

Expression conditions were determined by small-scale preparations. For large scale expression 500 ml cultures of 2× YT and 100 μg/ml ampicillin were inoculated with 5 ml over-night culture and grown at 37° C. Protein expression was induced at $OD_{600}$=0.5-1.3 by adding IPTG to a final concentration of 0.1 mM. Cultures producing SCCA1 were grown for 4-16 h, SCCA1/A2 for 16-18 h. Cultures producing the SCCA2 protein were induced at $OD_{600}$=1.2-1.4 and were grown for 2-3 h.

2.2. Protein Purification

Cells were harvested by centrifugation for 10 min at 2000 g, washed with 50 ml TE pH 8.0, and dissolved in 3 ml TE/g bacterial pellet. Lysozyme was added to a final concentration of 800 μg/g pellet and the mixtures were incubated on ice for 30-60 min and then frozen over night at −70° C. Magnesium chloride and DNase were added to a final concentration of 12 mM and 20 μg/g pellet, respectively. After incubation on ice for 30 min, samples were centrifuged for 30 min at 40000 g. To each supernatant 0.5 ml of 50% Glutathione Sepharose (Pharmacia) was added and incubated for 30 min-2 h at room temperature with gentle agitation. The slurry was washed 5-7 times using 1×PBS. GST-SCCA fusion protein was eluted using 0.5-1 ml Reduced Glutathione (Pharmacia) and incubated for 30-60 min at room temperature or over-night at 4° C., all with gentle agitation. SCCA protein was eluted by cleavage in between GST and SCCA. 0.48 ml cleavage buffer (50 mM Tris-HCl pH 7.0, 150 mM NaCl, 1 mM EDTA, 1 mM DTT) and 20 μl PreScission protease were added and samples were incubated at 4° C. with gentle agitation for 4 h or over-night. Proteins were analyzed on SDS-PAGE by Phast-system (Pharmacia).

2.3. Complex Binding

Complex binding of SCCA to substrates was performed by mixing 2 μg of SCCA-protein with 0.5 μg of Cathepsin G (Biodesign Int.) or 0.5 μg of 0.9 μg Cathepsin L (Calbiochem) in 1×PBS buffer in a total volume of 4.5 μl. Samples were incubated at 37° C. for 30 minutes. To each sample, 0.5 μl of 10× Complex-buffer (20% SDS, 140 mM Mercaptoethanol, bromophenolblue) was added. Samples were incubated for 3 minutes at 95° C. and analyzed on a 12.5% SDS-PAGE-gel. The SCCA1/A2 fusion protein forms a complex with Cathepsin G but not with Cathepsin L showing that the fusion protein is functional and has the substrate specificity of SCCA2.

Example 3

DNA Analysis 3.1. Southern Blot Analysis

Approximately 10 μg of DNA prepared from SCC cell-lines as well as from blood samples from normal healthy volunteers, were digested with restriction endonucleases PstI or BamHI. Digested DNA were separated on 0.8% agarose and transferred to membranes (Hybond N+, Pharmacia). Filters were prehybridized for 1 h and hybridized over night at 60° C. in 20 ml of a solution containing 5×SSC, 0.1% SDS, 5% Dextrane sulfate, Liquid block (Pharmacia) diluted 1:20 and salmon sperm DNA 100 μg/ml. Probe concentration during hybridization was 10 ng/ml. After hybridization filters were stringency washed for 15 min in 1×SSC/0.1% SDS and for 15 min in 0.2×SSC/1% SDS, both at 60° C. Probe hybridization was detected using Gene Images CDP-Star detection module (Pharmacia) with minor modifications. Filters were blocked for 1 hour at room temperature in a solution containing liquid block diluted 1:7.5. Then they were incubated in buffer A (0.1M Tris, 0.3M NaCl, pH 9.5)/0.5% BSA for 15 min before adding the anti-fluorescein HRP conjugate diluted 1:6800 and then incubated for another 45 min. Filters were washed for 3×10 min in buffer A/0.3% Tween 20 before adding detection reagent. Filters were incubated for 2 min, washed briefly in 2×SSC and wrapped in plastic film. Hyperfilm MP was exposed for 35 min.

3.2. Hybridization Probes

Probes were generated and labeled by PCR in a reaction containing 60 μm each of dATP, dCTP, and dGTP, 24 μM dTTP, 40 μM Fluorescein-11-dUTP, 2 mM $MgCl_2$, 3 μM forward primer, 3 μM backward primer, 15 ng DNA template (SCCA2-containing plasmid), 1 U Taq polymerase and 1×PCR buffer (Advanced Biotechnologies). Probe I: A 393 bp fragment of exon 8 (nucleotide 802-1194), primers SCCA 266-273F and SCCA 391-397B, Ta=50° C.; Probe II: A 126 bp fragment of exon 8 (nucleotide 957-1082), primers SCCA2 319-324F and SCCA2 357-363B, Ta=50° C.; probe III: A 1194 bp fragment covering the coding sequence and 22 nucleotides in the 3'-end of the gene, primers SCCA 1-7F and SCCA 391-397B, Ta=60° C.

Southern blot of PstI digested DNA hybridized with probe I show a different band pattern of DNA from a SCC-cell line compared to that of normal control DNA. DNA digested with BamHI also shows aberrant bands compared to normal control DNA.

3.3. PCR Analysis

DNA isolated by routine procedures from samples analysed by PCR using primers 7 and 8 (see Table 1) in a standard PCR-reaction show only product in samples containing the fusion gene.

Example 4

Hybridomas and Monoclonal Antibodies 4.1. Establishment of Hybridomas and Production of Monoclonal Antibodies Reactive with SCCA1/A2, SCCA2 and SCCA1

Polyclonal antisera reactive with SCC antigen was obtained by subcutaneous immunization of Rabbits with recombinant SCC antigen and collection of immune sera according to standard procedures. The titer of the polyclonal antisera was tested by determination of the reactivity of the antisera with biotinylated SCCA1/A2 and SCCA1 immobilized in streptavidin plates (Labsystems Oy, Helsinki, Finland), (FIG. 6). The recombinant SCCA1/A2 and SCCA1 were biotinylated with Biotin-N-succinimide caproate ester according to standard procedures.

Monoclonal antibodies reactive with SCCA1/A2 and SCCA2 were established by immunization of Balb/c mice intra peritoneally with 10-50 μg of recombinant SCCA1/A2 in Ribi adjuvant. After the immunization and 2-4 booster doses during 60-90 days spleen cells from the immunized mice were fused with P3×63Ag 8 myeloma cells as described (47).

Hybridomas producing antibodies reacting with SCCA1/A2 were selected by ELISA screening of hybridoma supernatants in microtiter wells coated with affinity purified polyclonal antiserum against mouse IgG+M, (Jackson Immuno Res Lab, US). The wells were then incubated with SCCA1/A2 antigen, and after washing the bound antigen was detected by incubation with polyclonal Rabbit Anti SCC and HRP labeled Swine Anti Rabbit Ig (Dako AS, Copenhagen, Denmark).

4.2. Reactivity of Selected Hybridomas with SCC Antigens

The reactivity of the established hybridomas was tested in an ELISA similar to the ELISA screening procedure. Briefly the monoclonal antibodies produced by the hybridomas were immobilized in microtiter plates coated with polyclonal antiserum against mouse IgG+M (Jackson Immuno Res Lab, US). The wells were then incubated with 50 μL of the different recombinant SCC antigens in PBS 1% BSA for 1 h, after washing the plates were incubated with 100 μL Rabbit anti-SCC diluted 1/5000 in PBS-1% BSA and incubated for additional 1 h. The bound Rabbit Anti-SCC was then detected by incubation with HRP-Swine anti Rabbit Ig and visualized with OPD substrate and determination of OD at 450 nm.

Figure 7:
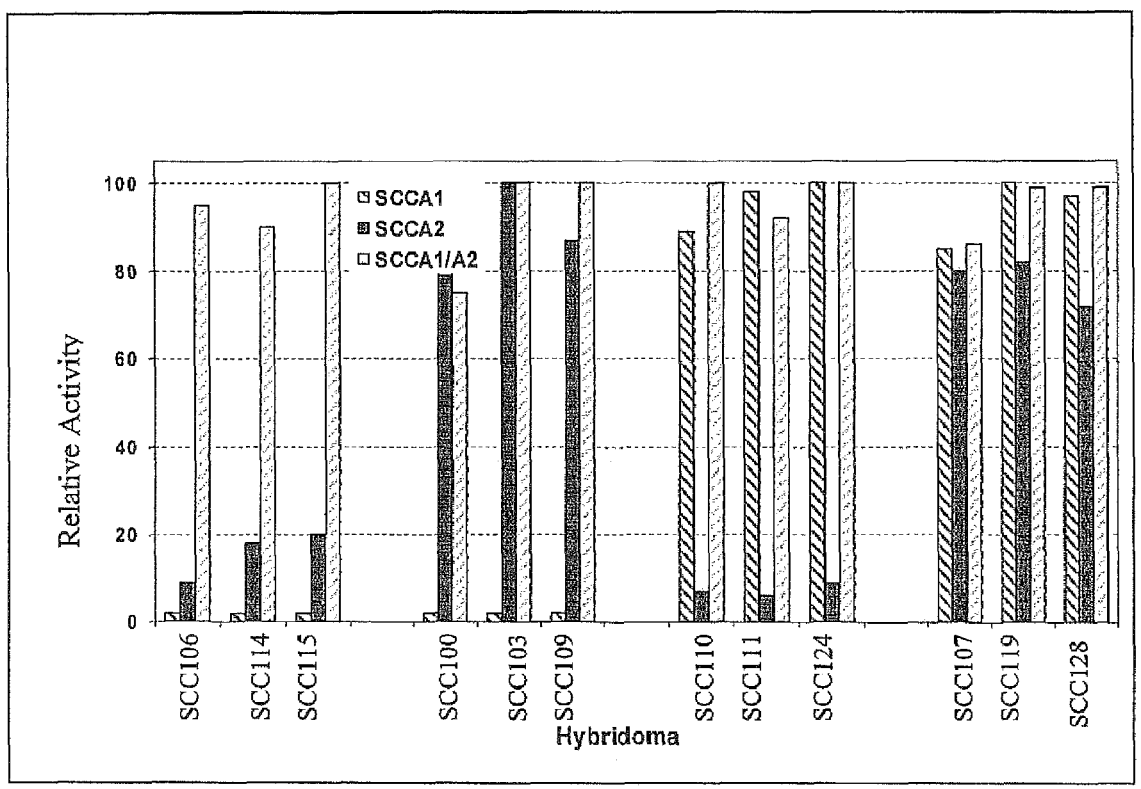
FIG. 7 is a graph showing the reactivity of established hybridomas with different SCC antigens.

In FIG. 7 the reactivity of selected hybridomas are shown. The SCC106, SCC114, SCC115 reacted only with SCCA1/A2, which indicate that they are specific for the SCCA1/A2 fusion protein. The SCC100, SCC103 and SCC109 reacted with SCCA2 and SCCA1/A2 but not with SCCA1 indicating that they are specific for SCCA2. The SCC110, SCC111 and SCC124 reacted with SCCA1 and SCCA1/A2 but not with SCCA2 suggesting that they are specific for SCCA1.

The SCC107, SCC119 and SCC128 reacted with all SCC antigens suggesting that they recognize a common epitope in SCCA1 and SCCA2.

Twice limiting dilution cloned clones producing antibodies reacting with SCCA1/A2, but negative for SCCA1 were produced.

Monoclonal antibodies were produced by in vitro cultivation of the hybridoma clones by inoculation of $10^4$ cells/mL in DMEM, 5% Fetal Calf Serum in roller bottles and allowed to grow for 10-14 days. The monoclonal antibodies were then purified from the culture medium by Protein A (Bioprocessing Ltd, Durham, UK) affinity chromatography according to the manufacturers recommendation.

Example 5

Using the established monoclonal antibodies and recombinant proteins it was possible to develop immunoassays for specific determination of SCCA1/A2 fusion protein and assays specific for SCCA2 and SCCA1 respectively.

5.1 Immunoassays for Determination of SCCA1/A2 Fusion Protein

Assays specific for SCCA1/A2 fusion protein but essentially negative for SCCA1 and SCCA2 were designed by using antibodies among SCC106, SCCC114 or SCC115 in combination with antibodies among SCC107, SCC119 or SCC128, see FIG. 7.

In the preferred configuration antibody SCC107 was used as catching antibody and SCC106 as detecting antibody.

SCC107 MAb was biotinylated with BiotinNHRS caproate ester, Sigma Chemical Co, US, using standard procedures, and used as catching antibody. SCC106 MAb were conjugated with HRP according to a modification of the Nakone procedure.

The biotinylated SCC107 MAb and HRP conjugated SCC106 MAb were used in two-site EIA according to the following protocol. Assay procedure
1. Add 50 μL of SCCA recombinant antigen (0-100 μg/L in PBS, 60 g/L BSA, pH 7.2)+100 μL of Biotin SCC107 MAb, 2 μg/mL, in Assay Buffer in Streptavidin coated microtiter plates, Labsystems Oy, Helsinki, Finland.
2. Incubate for 1 h±10 min with shaking
3. Wash 3 times with 5 mM Tris buffer, 0.05% Tween 40, pH 7.75.
4. Add 100 μL HRP SCC106 MAb, 2 μg/mL, in Assay Buffer.
5. Incubate for 1 h±10 min with shaking.
6. Wash 6 times with 5 mM Tris buffer, 0.05% Tween 40, pH 7.75.
7. Add 100 μL TMB, ELISA Technology, US.
8. Incubate 30 min±5 min
9. Determine OD 620 nm in ELISA reader.

Dose-response curves for SCCA1, SCCA2 and SCCA1/A2 antigens revealed that the assay was specific for the SCCA1/A2 recombinant antigen with <5% cross reactivity with SCCA1 or SCCA2.

5.2 Assays for Specific Determination of SCCA2

Assays specific for SCCA2 without significant reactivity with SCCA1/A2 and SCCA1 were designed by using antibodies among SCCϵ100, SCC103 or SCC109 in combination with antibodies among SCC107, SCC119 or SCC128. In the preferred configuration SCC107 MAb was used as catching antibody and the SCC103 was used as detecting antibody.

SCC107 MAb was biotinylated with BiotinNHRS caproate ester (Sigma Chemical Co, US) using standard procedures, and used as catching antibody. SCC103 MAb was conjugated with HRP, Type V (Sigma Chemical Co, US), according to a modification of the Nakone procedure.

The biotinylated SCC107 MAb and HRP conjugated SCC103 MAb were used in two-site EIA according to the following protocol.

Assay Procedure:
1. Add 50 μL of SCC recombinant antigen (0-100 μg/L in PBS, 60 g/L BSA, pH 7.2)+100 μL of Biotin SCC107 MAb, 2 μg/mL, in Assay Buffer in Streptavidin coated microtiter plates (Labsystems Oy, Helsinki, Finland).
2. Incubate for 1 h±10 min with shaking
3. Wash 3 times with 5 mM Tris buffer, 0.05% Tween 40, pH 7.75.
4. Add 100 μL HRP SCC103 MAb 2 μg/mL, in Assay Buffer.
5. Incubate for 1 h±10 min with shaking.
6. Wash 6 times with 5 mM Tris buffer, 0.05% Tween 40, pH 7.75.
7. Add 100 μL TMB, ELISA Technology, US
8. Incubate 30 min±5 min
9. Determine OD 620 nm in ELISA reader.

Based on the dose-response curves for SCCA2, SCCA1 and SCCA1/A2 fusion protein it was concluded that the assay according to example 5.2 was specific for SCCA2 with a cross-reactivity of <5% for SCCA1 and SCCA1/A2.

5.3. Assays for Specific Determination of SCCA1

Assays specific for SCCA1 without significant reactivity with SCCA2 and SCCA1/A2 were designed by using antibodies among SCC110, SCC111 or SCC124 in combination with antibodies of among SCC107, SCC119 or SCC128. In the preferred configurations SCC107MAb was used as catching antibody and SCC124 MAb was used as detecting antibody.

SCC107 MAb was biotinylated with BiotinNHRS caproate ester (Sigma Chemical Co, US) using standard procedures, and used as catching antibody. SCC124 MAb was conjugated with HRP, Type V, (Sigma Chemical Co., US) according to a modification of the Nakone procedure.

The biotinylated SCC107 MAb and HRP conjugated SCC124 MAb were used in two-site EIA according to the following protocol.

Assay Procedure
Add 50 μL of SCC antigen (0-100 μg/L in PBS, 60 g/L BSA, pH 7.2)+100 μL of Biotin SCC107 MAb, 2 μg/mL, in Assay Buffer in Streptavidin coated microtiter plates (Labsystems Oy, Helsinki, Finland).
2. Incubate for 1 h±10 min with shaking
3. Wash 3 times with 5 mM Tris buffer, 0.05% Tween 40, pH 7.75.
4. Add 100 μL HRP SCC124 MAb, 2 μg/mL, in Assay Buffer.
5. Incubate for 1 h±10 min with shaking.
6. Wash 6 times with 5 mM Tris buffer, 0.05% Tween 40, pH 7.75.
7. Add 100 μL TMB, (ELISA Technology, US).
8. Incubate 30 min±5 min
9. Determine OD 620 nm in ELISA reader.

Based on the antibodies according to 5.3 immunoassays specific for SCCA1 with <10 cross-reactivity for SCCA2 or SCCA1/A2 antigen may be designed.

The invention claimed is:

1. An isolated fusion transcript comprising exons from two different genes, wherein the fusion transcript is encoded by
    exons 2-7 of the Squamous Cell Carcinoma Antigen 1 (SCCA1) gene fused to exon 8 of the Squamous Cell Carcinoma Antigen 2 (SCCA2) gene, having the order exons 2-7 of SCCA1 followed by exon 8 of SCCA2, or exons 2-7 of the SCCA2 gene fused to exon 8 of the SCCA1 gene, having the order exons 2-7 of SCCA2 followed by exon 8 of SCCA1.

2. The isolated fusion transcript of claim 1, wherein the fusion transcript is isolated from Squamous Cell Carcinoma.

3. The isolated fusion transcript of claim 1, wherein the fusion transcript is encoded by SEQ ID NO: 11.

4. The isolated fusion transcript of claim 1, wherein the fusion transcript encodes a polypeptide comprising the amino acid sequence of SEQ ID NO: 1.

5. An isolated polynucleotide comprising the sequence set forth in SEQ ID NO: 11.

6. An isolated polynucleotide comprising exons 2-7 of SCCA2 fused to the exon 8 of SCCA1.

7. A plasmid comprising the polynucleotide of exons 2-7 of the SCCA1 gene fused to the polynucleotide of exon 8 of SCCA2 gene.

8. The plasmid of claim 7, comprising SEQ ID NO: 11.

9. A bacterium comprising the plasmid of claim 8.

10. An *E. coli* comprising the plasmid of claim 8.

* * * * *

SEQUENCE LISTING

<160> NUMBER OF SEQ ID NOS: 19

<210> SEQ ID NO 1
<211> LENGTH: 390
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 1

Met Asn Ser Leu Ser Glu Ala Asn Thr Lys Phe Met Phe Asp Leu Phe
  1               5                  10                  15

Gln Gln Phe Arg Lys Ser Lys Glu Asn Asn Ile Phe Tyr Ser Pro Ile
             20                  25                  30

Ser Ile Thr Ser Ala Leu Gly Met Val Leu Leu Gly Ala Lys Asp Asn
         35                  40                  45

Thr Ala Gln Gln Ile Lys Lys Val Leu His Phe Asp Gln Val Thr Glu
     50                  55                  60

Asn Thr Thr Gly Lys Ala Ala Thr Tyr His Val Asp Arg Ser Gly Asn
 65                  70                  75                  80

Val His His Gln Phe Gln Lys Leu Leu Thr Glu Phe Asn Lys Ser Thr
                 85                  90                  95

Asp Ala Tyr Glu Leu Lys Ile Ala Asn Lys Leu Phe Gly Glu Lys Thr
            100                 105                 110

Tyr Leu Phe Leu Gln Glu Tyr Leu Asp Ala Ile Lys Lys Phe Tyr Gln
        115                 120                 125

Thr Ser Val Glu Ser Val Asp Phe Ala Asn Ala Pro Glu Glu Ser Arg
    130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
                165                 170                 175

Val Asn Ala Ile Tyr Phe Lys Gly Gln Trp Glu Lys Lys Phe Asn Lys
            180                 185                 190

Glu Asp Thr Lys Glu Glu Lys Phe Trp Pro Asn Lys Asn Thr Tyr Lys
        195                 200                 205

Ser Ile Gln Met Met Arg Gln Tyr Thr Ser Phe His Phe Ala Ser Leu
    210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
                245                 250                 255

Leu Glu Glu Lys Leu Thr Ala Glu Lys Leu Met Glu Trp Thr Ser Leu
            260                 265                 270

Gln Asn Met Arg Glu Thr Cys Val Asp Leu His Leu Pro Arg Phe Lys
        275                 280                 285

Met Glu Glu Ser Tyr Asp Leu Lys Asp Thr Leu Arg Thr Met Gly Met
    290                 295                 300

Val Asn Ile Phe Asn Gly Asp Ala Asp Leu Ser Gly Met Thr Trp Ser
305                 310                 315                 320

His Gly Leu Ser Val Ser Lys Val Leu His Lys Ala Phe Val Glu Val
                325                 330                 335

Thr Glu Glu Gly Val Glu Ala Ala Ala Thr Ala Val Val Val Val
            340                 345                 350

Glu Leu Ser Ser Pro Ser Thr Asn Glu Glu Phe Cys Cys Asn His Pro
                355                 360                 365

Phe Leu Phe Phe Ile Arg Gln Asn Lys Thr Asn Ser Ile Leu Phe Tyr
        370                 375                 380

Gly Arg Phe Ser Ser Pro
385                 390

<210> SEQ ID NO 2
<211> LENGTH: 1193
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2

```
atgaattcac tcagtgaagc caacaccaag ttcatgttcg acctgttcca acagttcaga     60
aaatcaaaag agaacaacat cttctattcc cctatcagca tcacatcagc attagggatg    120
gtcctcttag gagccaaaga caacactgca caacagatta agaaggttct tcactttgat    180
caagtcacag agaacaccac aggaaaagct gcaacatatc atgttgatag gtcaggaaat    240
gttcatcacc agtttcaaaa gcttctgact gaattcaaca aattccactg atgcatatga    300
gctgaagatc gccaacaagc tcttcggaga aaaacgtat ctattttac aggaatattt    360 agatgccatc aagaaatttt accagaccag tgtggaatct gttgattttg caaatgctcc    420
agaagaaagt cgaagaaga ttaactcctg ggtggaaagt caaacgaatg aaaaaattaa    480
aaacctaatt cctgaaggta atattggcag caataccaca ttggttcttg tgaacgcaat    540
ctatttcaaa gggcagtggg agaagaaatt taataaagaa gatactaaag gagaaaaatt    600
ttggccaaac aagaatacat acaagtccat acagatgatg aggcaataca catcttttca    660
ttttgcctcg ctggaggatg tacaggccaa ggtcctggaa ataccataca aaggcaaaga    720
tctaagcatg attgtgttgc tgccaaatga aatcgatggt ctccagaagc ttgaagagaa    780
actcactgct gagaaattga tggaatggac aagtttgcag aatatgagag agacatgtgt    840
cgatttacac ttacctcggt tcaaaatgga agagagctat gacctcaagg acacgttgag    900
aaccatggga atggtgaata tcttcaatgg ggatgcagac ctctcaggca tgacctggag    960
ccacggtctc tcagtatcta agtcctaca caaggccttt gtggaggtca ctgaggaggg   1020
agtggaagct gcagctgcca ccgctgtagt agtagtcgaa ttatcatctc cttcaactaa   1080
tgaagagttc tgttgtaatc accctttcct attcttcata aggcaaaata agaccaacag   1140
catcctcttc tatggcagat tctcatcccc atagatgcaa ttagtgtgtc act          1193
```

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgggatccat gaattcactc agtgaagcc                                       29

<210> SEQ ID NO 4
<211> LENGTH: 38
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 4
gagctcgagt ctcatcagtg acagactaat tgcatcta                              38

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tggaatggac aagtttgcag                                                  20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtaggactcc agatagcac                                                   19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tggagccacg gtctctcag                                                   19

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
attagttgaa ggagatgata attc                                             24

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatacataca agtcca                                                      16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 10
ggactttaga tactga                                                    16

<210> SEQ ID NO 11
<211> LENGTH: 1170
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 11
atgaattcac tcagtgaagc caacaccaag ttcatgttcg acctgttcca acagttcaga      60
aaatcaaaag agaacaacat cttctattcc cctatcagca tcacatcagc attagggatg    120
gtcctcttag agccaaaga caacactgca caacagatta agaaggttct tcactttgat    180
caagtcacag agaacaccac aggaaaagct gcaacatatc atgttgatag gtcaggaaat    240
gttcatcacc agtttcaaaa gcttctgact gaattcaaca atccactga tgcatatgag    300 ctgaagatcg ccaacaagct cttcggagaa aaacgtatc tattttaca ggaatattta    360 gatgccatca agaaattta ccagaccagt gtggaatctg ttgattttgc aaatgctcca    420
gaagaaagtc gaaagaagat taactcctgg gtggaaagtc aaacgaatga aaaaattaaa    480
aacctaattc ctgaaggtaa tattggcagc aataccacat tggttcttgt gaacgcaatc    540
tatttcaaag gcagtgggga gaagaaattt aataagaag atactaaaga ggaaaaattt    600
tggccaaaca agaatacata caagtccata cagatgatga ggcaatacac atctttcat    660 tttgcctcgc tggaggatgt acaggccaag gtcctggaaa taccatacaa aggcaaagat    720
ctaagcatga ttgtgttgct gccaaatgaa atcgatggtc tccagaagct tgaagagaaa    780
ctcactgctg agaaattgat ggaatggaca agtttgcaga atatgagaga gacatgtgtc    840
gatttacact tacctcggtt caaaatggaa agagctatg acctcaagga cacgttgaga    900
accatgggaa tggtgaatat cttcaatggg gatgcagacc tctcaggcat gacctggagc    960
cacggtctct cagtatctaa agtcctacac aaggcctttg tggaggtcac tgaggaggga    1020
gtggaagctg cagctgccac cgctgtagta gtagtcgaat tatcatctcc ttcaactaat    1080
gaagagttct gttgtaatca cccttttccta ttcttcataa ggcaaaataa gaccaacagc    1140
atcctcttct atggcagatt ctcatcccca                                      1170

<210> SEQ ID NO 12
<211> LENGTH: 1173
<212> TYPE: DNA
<213> ORGANISM: Homo sapiens

<400> SEQUENCE: 12
atgaattcac tcagtgaagc caacaccaag ttcatgttcg acctgttcca acagttcaga      60
aaatcaaaag agaacaacat cttctattcc cctatcagca tcacatcagc attagggatg    120
gtcctcttag agccaaaga caacactgca caacagatta agaaggttct tcactttgat    180
caagtcacag agaacaccac aggaaaagct gcaacatatc atgttgatag gtcaggaaat    240
gttcatcacc agtttcaaaa gcttctgact gaattcaaca atccactga tgcatatgag    300 ctgaagatcg ccaacaagct cttcggagaa aaacgtatc tattttaca ggaatattta    360 gatgccatca agaaattta ccagaccagt gtggaatctg ttgattttgc aaatgctcca    420
gaagaaagtc gaaagaagat taactcctgg gtggaaagtc aaacgaatga aaaaattaaa    480

```
aacctaattc ctgaaggtaa tattggcagc aataccacat tggttcttgt gaacgcaatc        540
tatttcaaag ggcagtggga gaagaaattt aataaagaag atactaaaga ggaaaaattt        600
tggccaaaca agaatacata caagtccata cagatgatga ggcaatacac atctttcat         660 tttgcctcgc tggaggatgt acaggccaag gtcctggaaa taccatacaa aggcaaagat        720
ctaagcatga ttgtgttgct gccaaatgaa atcgatggtc tccagaagct tgaagagaaa        780
ctcactgctg agaaattgat ggaatggaca agtttgcaga atatgagaga gacacgtgtc        840
gatttacact tacctcggtt caaagtggaa gagagctatg acctcaagga cacgttgaga        900
accatgggaa tggtggatat cttcaatggg gatgcagacc tctcaggcat gaccgggagc        960
cgcggtctcg tgctatctgg agtcctacac aaggcctttg tggaggttac agaggaggga       1020
gcagaagctg cagctgccac cgctgtagta ggattcggat catcacctac ttcaactaat       1080
gaagagttcc attgtaatca ccctttccta ttcttcataa ggcaaaataa gaccaacagc       1140
atcctcttct atggcagatt ctcatccccg tag                                    1173

<210> SEQ ID NO 13
<211> LENGTH: 1173
<212> TYPE: DNA
<213> ORGANISM: Homo sapiens

<400> SEQUENCE: 13
atgaattcac tcagtgaagc caacaccaag ttcatgttcg atctgttcca acagttcaga         60
aaatcaaaag agaacaacat cttctattcc cctatcagca tcacatcagc attagggatg        120
gtcctcttag gagccaaaga caacactgca caacaaatta gcaaggttct tcactttgat        180
caagtcacag agaacaccac agaaaaagct gcaacatatc atgttgatag gtcaggaaat        240
gttcatcacc agtttcaaaa gcttctgact gaattcaaca atccactga tgcatatgag         300 ctgaagatcg ccaacaagct cttcggagaa aagacgtatc aatttttaca ggaatattta        360
gatgccatca agaaattta ccagaccagt gtggaatcta ctgattttgc aaatgctcca        420
gaagaaagtc gaagaagat taactcctgg gtggaaagtc aaacgaatga aaaaattaaa        480
aacctatttc ctgatgggac tattggcaat gatacgcaca tggttcttgt gaacgcaatc       540
tatttcaaag ggcagtggga gaataaattt aaaaagaaa acactaaaga ggaaaaattt        600
tggccaaaca agaatacata caaatctgta cagatgatga ggcaatacaa ttcctttaat       660
tttgccttgc tggaggatgt acaggccaag gtcctggaaa taccatacaa aggcaaagat        720
ctaagcatga ttgtgctgct gccaaatgaa atcgatggtc tgcagaagct tgaagagaaa        780
ctcactgctg agaaattgat ggaatggaca agtttgcaga atatgagaga gacatgtgtc        840
gatttacact tacctcggtt caaaatgaa gagagctatg acctcaagga cacgttgaga         900
accatgggaa tggtgaatat cttcaatggg gatgcagacc tctcaggcat gacctggagc        960
cacggtctct cagtatctaa agtcctacac aaggcctttg tggaggtcac tgaggaggga       1020
gtggaagctg cagctgccac cgctgtagta gtagtcgaat tatcatctcc ttcaactaat       1080
gaagagttct gttgtaatca ccctttccta ttcttcataa ggcaaaataa gaccaacagc       1140
atcctcttct atggcagatt ctcatcccca tag                                    1173

<210> SEQ ID NO 14
<211> LENGTH: 390
<212> TYPE: PRT
<213> ORGANISM: Homo sapiens

<400> SEQUENCE: 14
```

-continued

Met Asn Ser Leu Ser Glu Ala Asn Thr Lys Phe Met Phe Asp Leu Phe
 1               5                   10                  15

Gln Gln Phe Arg Lys Ser Lys Glu Asn Asn Ile Phe Tyr Ser Pro Ile
             20                  25                  30

Ser Ile Thr Ser Ala Leu Gly Met Val Leu Leu Gly Ala Lys Asp Asn
         35                  40                  45

Thr Ala Gln Gln Ile Lys Lys Val Leu His Phe Asp Gln Val Thr Glu
     50                  55                  60

Asn Thr Thr Gly Lys Ala Ala Thr Tyr His Val Asp Arg Ser Gly Asn
 65                  70                  75                  80

Val His His Gln Phe Gln Lys Leu Leu Thr Glu Phe Asn Lys Ser Thr
             85                  90                  95

Asp Ala Tyr Glu Leu Lys Ile Ala Asn Lys Leu Phe Gly Glu Lys Thr
            100                 105                 110

Tyr Leu Phe Leu Gln Glu Tyr Leu Asp Ala Ile Lys Lys Phe Tyr Gln
        115                 120                 125

Thr Ser Val Glu Ser Val Asp Phe Ala Asn Ala Pro Glu Glu Ser Arg
    130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
            165                 170                 175

Val Asn Ala Ile Tyr Phe Lys Gly Gln Trp Glu Lys Lys Phe Asn Lys
        180                 185                 190

Glu Asp Thr Lys Glu Glu Lys Phe Trp Pro Asn Lys Asn Thr Tyr Lys
    195                 200                 205

Ser Ile Gln Met Met Arg Gln Tyr Thr Ser Phe His Phe Ala Ser Leu
210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
            245                 250                 255

Leu Glu Glu Lys Leu Thr Ala Glu Lys Leu Met Glu Trp Thr Ser Leu
        260                 265                 270

Gln Asn Met Arg Glu Thr Arg Val Asp Leu His Leu Pro Arg Phe Lys
    275                 280                 285

Val Glu Glu Ser Tyr Asp Leu Lys Asp Thr Leu Arg Thr Met Gly Met
290                 295                 300

Val Asp Ile Phe Asn Gly Asp Ala Asp Leu Ser Gly Met Thr Gly Ser
305                 310                 315                 320

Arg Gly Leu Val Leu Ser Gly Val Leu His Lys Ala Phe Val Glu Val
            325                 330                 335

Thr Glu Glu Gly Ala Glu Ala Ala Ala Ala Thr Ala Val Val Gly Phe
        340                 345                 350

Gly Ser Ser Pro Ala Ser Thr Asn Glu Glu Phe His Cys Asn His Pro
    355                 360                 365

Phe Leu Phe Phe Ile Arg Gln Asn Lys Thr Asn Ser Ile Leu Phe Tyr
370                 375                 380

Gly Arg Phe Ser Ser Pro
385                 390

<210> SEQ ID NO 15
<211> LENGTH: 390
<212> TYPE: PRT
<213> ORGANISM: Homo sapiens

<400> SEQUENCE: 15

```
Met Asn Ser Leu Ser Glu Ala Asn Thr Lys Phe Met Phe Asp Leu Phe
  1               5                  10                  15

Gln Gln Phe Arg Lys Ser Lys Glu Asn Asn Ile Phe Tyr Ser Pro Ile
             20                  25                  30

Ser Ile Thr Ser Ala Leu Gly Met Val Leu Leu Gly Ala Lys Asp Asn
         35                  40                  45

Thr Ala Gln Gln Ile Ser Lys Val Leu His Phe Asp Gln Val Thr Glu
     50                  55                  60

Asn Thr Thr Glu Lys Ala Ala Thr Tyr His Val Asp Arg Ser Gly Asn
 65                  70                  75                  80

Val His His Gln Phe Gln Lys Leu Leu Thr Glu Phe Asn Lys Ser Thr
                 85                  90                  95

Asp Ala Tyr Glu Leu Lys Ile Ala Asn Lys Leu Phe Gly Glu Lys Thr
            100                 105                 110

Tyr Gln Phe Leu Gln Glu Tyr Leu Asp Ala Ile Lys Lys Phe Tyr Gln
        115                 120                 125

Thr Ser Val Glu Ser Thr Asp Phe Ala Asn Ala Pro Glu Glu Ser Arg
    130                 135                 140

Lys Lys Ile Asn Ser Trp Val Glu Ser Gln Thr Asn Glu Lys Ile Lys
145                 150                 155                 160

Asn Leu Phe Pro Asp Gly Thr Ile Gly Asn Asp Thr Thr Leu Val Leu
                165                 170                 175

Val Asn Ala Ile Tyr Phe Lys Gly Gln Trp Glu Asn Lys Phe Lys Lys
            180                 185                 190

Glu Asn Thr Lys Glu Glu Lys Phe Trp Pro Asn Lys Asn Thr Tyr Lys
        195                 200                 205

Ser Val Gln Met Met Arg Gln Tyr Asn Ser Phe Asn Phe Ala Leu Leu
    210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
                245                 250                 255

Leu Glu Glu Lys Leu Thr Ala Glu Lys Leu Met Glu Trp Thr Ser Leu
            260                 265                 270

Gln Asn Met Arg Glu Thr Cys Val Asp Leu His Leu Pro Arg Phe Lys
        275                 280                 285

Met Glu Glu Ser Tyr Asp Leu Lys Asp Thr Leu Arg Thr Met Gly Met
290                 295                 300

Val Asn Ile Phe Asn Gly Asp Ala Asp Leu Ser Gly Met Thr Trp Ser
305                 310                 315                 320

His Gly Leu Ser Val Ser Lys Val Leu His Lys Ala Phe Val Glu Val
                325                 330                 335

Thr Glu Glu Gly Val Glu Ala Ala Ala Thr Ala Val Val Val Val
            340                 345                 350

Glu Leu Ser Ser Pro Ser Thr Asn Glu Glu Phe Cys Cys Asn His Pro
        355                 360                 365

Phe Leu Phe Phe Ile Arg Gln Asn Lys Thr Asn Ser Ile Leu Phe Tyr
    370                 375                 380

Gly Arg Phe Ser Ser Pro
385                 390
```

<210> SEQ ID NO 16

```
<211> LENGTH: 1173
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 16
atgaattcac tcagtgaagc caacaccaag ttcatgttcg acctgttcca acagttcaga      60
aaatcaaaag agaacaacat cttctattcc cctatcagca tcacatcagc attagggatg    120
gtcctcttag gagccaaaga caacactgca aacagatta agaaggttct tcactttgat     180
caagtcacag agaacaccac aggaaaagct gcaacatatc atgttgatag gtcaggaaat    240
gttcatcacc agtttcaaaa gcttctgact gaattcaaca atccactga tgcatatgag     300 ctgaagatcg ccaacaagct cttcggagaa aaacgtatc tattttttaca ggaatattta    360 gatgccatca agaattttta ccagaccagt gtggaatctg ttgattttgc aaatgctcca    420
gaagaaagtc gaagaagat taactcctgg gtggaaagtc aaacgaatga aaaaattaaa    480
aacctaattc ctgaaggtaa tattggcagc aataccacat tggttcttgt gaacgcaatc    540
tatttcaaag gcagtgggga aagaaattt aataagaag atactaaaga ggaaaaattt     600
tggccaaaca gaatacata caartcyrta cagatgatga ggcaatacam wtcytttmat    660
tttgcctygc tggaggatgt acaggccaag gtcctggaaa taccatacaa aggcaaagat    720
ctaagcatga ttgtgytgct gccaaatgaa atcgatggtc tscagaagct tgaagagaaa    780
ctcactgctg agaaattgat ggaatggaca agtttgcaga atatgagaga dacaygtgtc    840
gatttacact tacctcggtt caaartggaa gagagctatg acctcaagga cacgttgaga    900
accatgggaa tggtgratat cttcaatggg gatgcagacc tctcaggcat gacckggagc    960
crcggtctck yrstatctrr agtcctacac aaggcctttg tggaggtyac wgaggaggga  1020
gyrgaagctg cagctgccac cgctgtagta gtagtcgaat tatcatctcc ttcaactaat  1080
gaagagttct gttgtaatca ccctttccta ttcttcataa ggcaaaataa gaccaacagc  1140
atcctcttct atggcagatt ctcatcccca tag                               1173

<210> SEQ ID NO 17
<211> LENGTH: 390
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (210)
<223> OTHER INFORMATION: Ile or Val
<220> FEATURE:
<221> NAME/KEY: MOD_RES
<222> LOCATION: (217)
<223> OTHER INFORMATION: Thr or Asn
<220> FEATURE:
<221> NAME/KEY: MOD_RES
<222> LOCATION: (220)
<223> OTHER INFORMATION: His or Asn
<220> FEATURE:
<221> NAME/KEY: MOD_RES
<222> LOCATION: (223)
<223> OTHER INFORMATION: Ser or Leu
<220> FEATURE:
<221> NAME/KEY: MOD_RES
<222> LOCATION: (279)
<223> OTHER INFORMATION: Arg or Cys
<220> FEATURE:
<221> NAME/KEY: MOD_RES
<222> LOCATION: (289)
```

```
<223> OTHER INFORMATION: Val or Met
<220> FEATURE:
<221> NAME/KEY: MOD_RES
<222> LOCATION: (306)
<223> OTHER INFORMATION: Asp or Asn
<220> FEATURE:
<221> NAME/KEY: MOD_RES
<222> LOCATION: (319)
<223> OTHER INFORMATION: Gly or Trp
<220> FEATURE:
<221> NAME/KEY: MOD_RES
<222> LOCATION: (321)
<223> OTHER INFORMATION: Arg or His
<220> FEATURE:
<221> NAME/KEY: MOD_RES
<222> LOCATION: (324)
<223> OTHER INFORMATION: Val or Ser
<220> FEATURE:
<221> NAME/KEY: MOD_RES
<222> LOCATION: (325)
<223> OTHER INFORMATION: Leu or Val
<220> FEATURE:
<221> NAME/KEY: MOD_RES
<222> LOCATION: (327)
<223> OTHER INFORMATION: Gly or Lys
<220> FEATURE:
<221> NAME/KEY: MOD_RES
<222> LOCATION: (341)
<223> OTHER INFORMATION: Ala or Val

<400> SEQUENCE: 17

Met Asn Ser Leu Ser Glu Ala Asn Thr Lys Phe Met Phe Asp Leu Phe
 1               5                  10                  15

Gln Gln Phe Arg Lys Ser Lys Glu Asn Asn Ile Phe Tyr Ser Pro Ile
            20                  25                  30

Ser Ile Thr Ser Ala Leu Gly Met Val Leu Leu Gly Ala Lys Asp Asn
        35                  40                  45

Thr Ala Gln Gln Ile Lys Lys Val Leu His Phe Asp Gln Val Thr Glu
    50                  55                  60

Asn Thr Thr Gly Lys Ala Ala Thr Tyr His Val Asp Arg Ser Gly Asn
 65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
           100                 105                 110

Tyr Leu Phe Leu Gln Glu Tyr Leu Asp Ala Ile Lys Lys Phe Tyr Gln
       115                 120                 125

Thr Ser Val Glu Ser Val Asp Phe Ala Asn Ala Pro Glu Glu Ser Arg
   130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
               165                 170                 175

Val Asn Ala Ile Tyr Phe Lys Gly Gln Trp Glu Lys Lys Phe Asn Lys
           180                 185                 190

Glu Asp Thr Lys Glu Glu Lys Phe Trp Pro Asn Lys Asn Thr Tyr Lys
       195                 200                 205

Ser Xaa Gln Met Met Arg Gln Tyr Xaa Ser Phe Xaa Phe Ala Xaa Leu
   210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
               245                 250                 255
```

```
Leu Glu Glu Lys Leu Thr Ala Glu Lys Leu Met Glu Trp Thr Ser Leu
            260                 265                 270

Gln Asn Met Arg Glu Thr Xaa Val Asp Leu His Leu Pro Arg Phe Lys
        275                 280                 285

Xaa Glu Glu Ser Tyr Asp Leu Lys Asp Thr Leu Arg Thr Met Gly Met
    290                 295                 300

Val Xaa Ile Phe Asn Gly Asp Ala Asp Leu Ser Gly Met Thr Xaa Ser
305                 310                 315                 320

Xaa Gly Leu Xaa Xaa Ser Xaa Val Leu His Lys Ala Phe Val Glu Val
                325                 330                 335

Thr Glu Glu Gly Xaa Glu Ala Ala Ala Thr Ala Val Val Val
            340                 345                 350

Glu Leu Ser Ser Pro Ser Thr Asn Glu Glu Phe Cys Cys Asn His Pro
            355                 360                 365

Phe Leu Phe Phe Ile Arg Gln Asn Lys Thr Ser Ile Leu Phe Tyr
            370                 375                 380

Gly Arg Phe Ser Ser Pro
385                 390

<210> SEQ ID NO 18
<211> LENGTH: 1173
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 18
atgaattcac tcagtgaagc caacaccaag ttcatgttcg atctgttcca acagttcaga      60
aaatcaaaag agaacaacat cttctattcc cctatcagca tcacatcagc attagggatg    120
gtcctcttag gagccaaaga caacactgca caacaaatta gcaaggttct tcactttgat    180
caagtcacag agaacaccac agaaaaagct gcaacatatc atgttgatag gtcaggaaat    240
gttcatcacc agtttcaaaa gcttctgact gaattcaaca atccactga tgcatatgag     300 ctgaagatcg ccaacaagct cttcggagaa agacgtatc aattttttaca ggaatattta    360 gatgccatca gaaatttta ccagaccagt gtggaatcta ctgatttgc aaatgctcca     420 gaagaaagtc gaaagaagat taactcctgg gtggaaagtc aaacgaatga aaaaattaaa    480
aacctatttc ctgatgggac tattggcaat gatacgacac tggttcttgt gaacgcaatc    540
tatttcaaag gcagtgggga aataaattt aaaaagaaa cactaaaga ggaaaaattt       600 tggccaaaca gaatacata caartcyrta cagatgatga ggcaatacam wtcytttat     660 tttgcctygc tggaggatgt acaggccaag gtcctggaaa taccatacaa aggcaaagat    720
ctaagcatga ttgtgytgct gccaaatgaa atcgatggtc tscagaagct tgaagagaaa   780
ctcactgctg agaaattgat ggaatggaca agtttgcaga atatgagaga acaygtgtc     840 gatttacact tacctcggtt caaartggaa agagcatatg acctcaagga cacgttgaga    900
accatgggaa tggtgratat cttcaatggg gatgcagacc tctcaggcat gacckggagc    960
crcggtctck yrstatctrr agtcctacac aaggcctttg tggaggtyac wgaggaggga    1020
gyrgaagctg cagctgccac cgctgtagta ggattcggat catcacctac ttcaactaat   1080
gaagagttcc attgtaatca ccctttccta ttcttcataa ggcaaaataa gaccaacagc   1140
atcctcttct atggcagatt ctcatccccg tag                                1173

<210> SEQ ID NO 19
```

```
<211> LENGTH: 390
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (210)
<223> OTHER INFORMATION: Ile or Val
<220> FEATURE:
<221> NAME/KEY: MOD_RES
<222> LOCATION: (217)
<223> OTHER INFORMATION: Thr or Asn
<220> FEATURE:
<221> NAME/KEY: MOD_RES
<222> LOCATION: (220)
<223> OTHER INFORMATION: His or Asn
<220> FEATURE:
<221> NAME/KEY: MOD_RES
<222> LOCATION: (223)
<223> OTHER INFORMATION: Ser or Leu
<220> FEATURE:
<221> NAME/KEY: MOD_RES
<222> LOCATION: (279)
<223> OTHER INFORMATION: Arg or Cys
<220> FEATURE:
<221> NAME/KEY: MOD_RES
<222> LOCATION: (289)
<223> OTHER INFORMATION: Val or Met
<220> FEATURE:
<221> NAME/KEY: MOD_RES
<222> LOCATION: (306)
<223> OTHER INFORMATION: Asp or Asn
<220> FEATURE:
<221> NAME/KEY: MOD_RES
<222> LOCATION: (319)
<223> OTHER INFORMATION: Gly or Trp
<220> FEATURE:
<221> NAME/KEY: MOD_RES
<222> LOCATION: (321)
<223> OTHER INFORMATION: Arg or His
<220> FEATURE:
<221> NAME/KEY: MOD_RES
<222> LOCATION: (324)
<223> OTHER INFORMATION: Val or Ser
<220> FEATURE:
<221> NAME/KEY: MOD_RES
<222> LOCATION: (325)
<223> OTHER INFORMATION: Leu or Val
<220> FEATURE:
<221> NAME/KEY: MOD_RES
<222> LOCATION: (327)
<223> OTHER INFORMATION: Gly or Lys
<220> FEATURE:
<221> NAME/KEY: MOD_RES
<222> LOCATION: (341)
<223> OTHER INFORMATION: Ala or Val

<400> SEQUENCE: 19

Met Asn Ser Leu Ser Glu Ala Asn Thr Lys Phe Met Phe Asp Leu Phe
  1               5                  10                  15

Gln Gln Phe Arg Lys Ser Lys Glu Asn Asn Ile Phe Tyr Ser Pro Ile
                 20                  25                  30

Ser Ile Thr Ser Ala Leu Gly Met Val Leu Leu Gly Ala Lys Asp Asn
             35                  40                  45

Thr Ala Gln Gln Ile Ser Lys Val Leu His Phe Asp Gln Val Thr Glu
         50                  55                  60

Asn Thr Thr Glu Lys Ala Ala Thr Tyr His Val Asp Arg Ser Gly Asn
 65                  70                  75                  80

Val His His Gln Phe Gln Lys Leu Leu Thr Glu Phe Asn Lys Ser Thr
                 85                  90                  95

Asp Ala Tyr Glu Leu Lys Ile Ala Asn Lys Leu Phe Gly Glu Lys Thr
```

```
                    100                 105                 110
Tyr Gln Phe Leu Gln Glu Tyr Leu Asp Ala Ile Lys Lys Phe Tyr Gln
        115                 120                 125

Thr Ser Val Glu Ser Thr Asp Phe Ala Asn Ala Pro Glu Glu Ser Arg
    130                 135                 140

Lys Lys Ile Asn Ser Trp Val Glu Ser Gln Thr Asn Glu Lys Ile Lys
145                 150                 155                 160

Asn Leu Phe Pro Asp Gly Thr Ile Gly Asn Asp Thr Thr Leu Val Leu
            165                 170                 175

Val Asn Ala Ile Tyr Phe Lys Gly Gln Trp Glu Asn Lys Phe Lys Lys
                180                 185                 190

Glu Asn Thr Lys Glu Lys Phe Trp Pro Asn Lys Asn Thr Tyr Lys
        195                 200                 205

Ser Xaa Gln Met Met Arg Gln Tyr Xaa Ser Phe Xaa Phe Ala Xaa Leu
    210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
            245                 250                 255

Leu Glu Glu Lys Leu Thr Ala Glu Lys Leu Met Glu Trp Thr Ser Leu
            260                 265                 270

Gln Asn Met Arg Glu Thr Xaa Val Asp Leu His Leu Pro Arg Phe Lys
        275                 280                 285

Xaa Glu Glu Ser Tyr Asp Leu Lys Asp Thr Leu Arg Thr Met Gly Met
    290                 295                 300

Val Xaa Ile Phe Asn Gly Asp Ala Asp Leu Ser Gly Met Thr Xaa Ser
305                 310                 315                 320

Xaa Gly Leu Xaa Xaa Ser Xaa Val Leu His Lys Ala Phe Val Glu Val
            325                 330                 335

Thr Glu Glu Gly Xaa Glu Ala Ala Ala Thr Ala Val Val Gly Phe
            340                 345                 350

Gly Ser Ser Pro Ala Ser Thr Asn Glu Glu Phe His Cys Asn His Pro
        355                 360                 365

Phe Leu Phe Phe Ile Arg Gln Asn Lys Thr Asn Ser Ile Leu Phe Tyr
    370                 375                 380

Gly Arg Phe Ser Ser Pro
385             390
```